United States Patent [19]

Josephy et al.

[11] Patent Number: 5,104,894

[45] Date of Patent: Apr. 14, 1992

[54] ELLAGIC ACID ANALOGUES

[75] Inventors: Philip D. Josephy, Guelph; Victor A. Snieckus, Waterloo, both of Canada

[73] Assignee: University of Guelph, Ontario, Canada

[21] Appl. No.: 165,471

[22] Filed: Mar. 8, 1988

[51] Int. Cl.⁵ .................... A61K 31/35; C07D 311/08
[52] U.S. Cl. .................................. 514/455; 549/280
[58] Field of Search ........................ 549/280; 514/455

[56] References Cited

FOREIGN PATENT DOCUMENTS 591473 2/1978 U.S.S.R.
2084578 4/1982 United Kingdom.

OTHER PUBLICATIONS

CA 26456p, vol. 78, 1973.
CA 57523v., vol. 82(9).

Primary Examiner—Jane T. Fan
Attorney, Agent, or Firm—Bell, Seltzer, Park & Gibson

[57] ABSTRACT

Synthetic novel ellagic acid congeners of the formula:

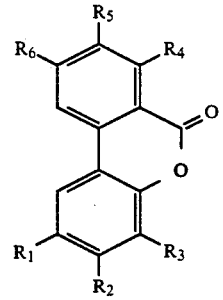

wherein:
$R_1$ is —H, —OH or —OR';
$R_2$ is —H, —OH or —OR';
$R_3$ is —H, —OH or —OR';
$R_4$ is —H, —OH or —OR';
$R_5$ is —H, —OH or —OR';
$R_6$ is —H, —OH or —OR';
R' is lower alkyl having 1 to 8 carbon atoms or —CH$_2$—Ar;
Ar is phenyl or substituted phenyl, and at least one of $R_1$, $R_2$, $R_3$, $R_4$, $R_5$ and $R_6$ is other than —H. The above compounds and 6H-dibenzo[b,d]pyran-6-one are useful for inhibiting mutagenic activity in living cells.

18 Claims, 1 Drawing Sheet

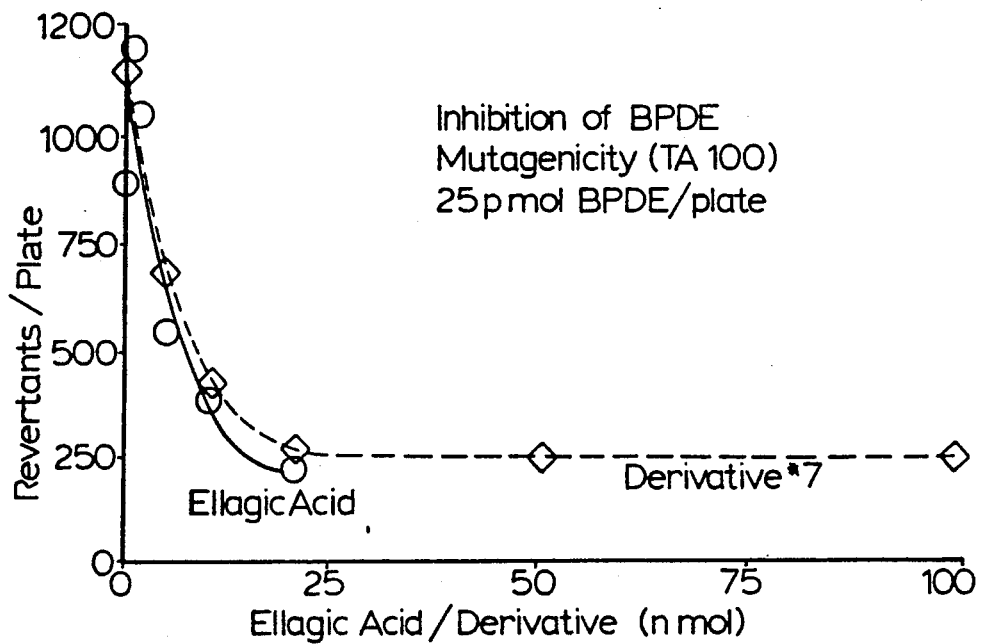
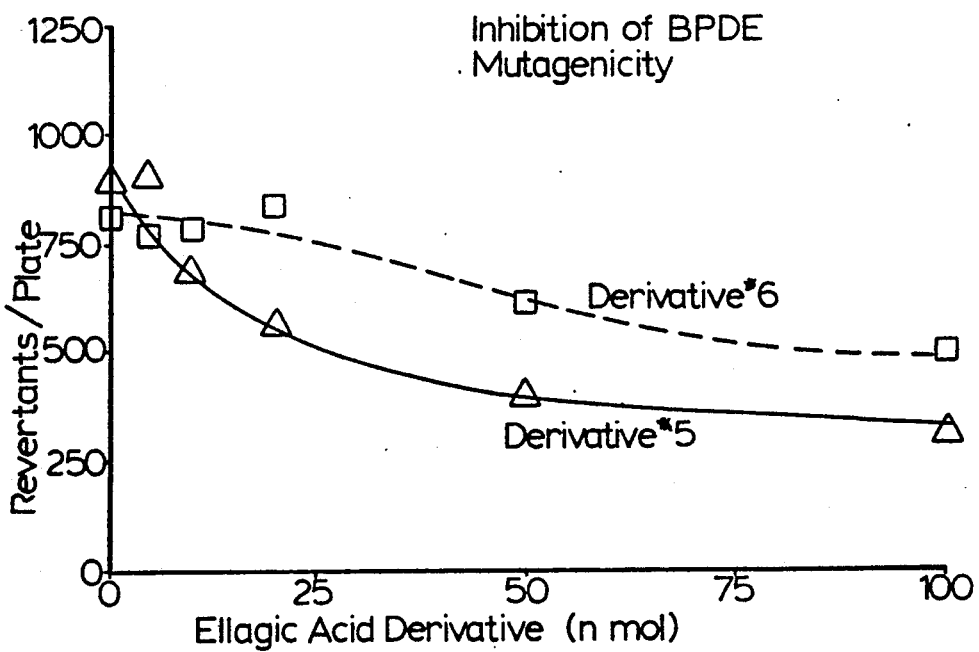

ELLAGIC ACID ANALOGUES

FIELD OF THE INVENTION

This invention relates to synthetic compounds useful in inhibition of mutagenis and chemotherapy and in particular, relates to synthetic ellagic acid congeners for derivatives.

BACKGROUND OF THE INVENTION

Ellagic acid is a natural product found in certain fruits, such as strawberries, which has been demonstrated to be effective as an inhibitor of polycyclic aromatic hydrocarbons and dialkyl nitrosamines-induced mutagenesis. In 1982 Wood et al (PNAS: 79: 5513) demonstrated that ellagic acid is a potent inhibitor of the mutagenic activity of benzo[a]pyrine-7,8-dihydrodiol-1,10-epoxide (BPDE) in the well known Ames test.

It has been found, however, by Smart et al *Carbinogenesis* 7: 1663-16667, 1986 that ellagic acid suffers from very poor pharmacokenetics particularly with respect to poor absorption characteristics from the gastro-intestinal tract and subsequent rapid elimination.

SUMMARY OF THE INVENTION

In accordance with an aspect of this invention, novel ellagic acid derivatives or congeners are provided. The novel derivatives are those represented by the group of the following formula:

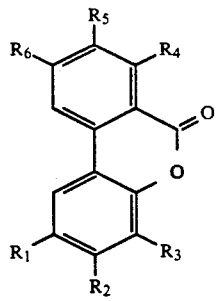

I wherein:
$R_2$ is —H, —OH or —OR';
$R_3$ is —H, —OH or —OR';
$R_4$ is —H, —OH or —OR';
$R_5$ is —H, —OH or —OR';
$R_6$ is —H, —OH or —OR';
R' is lower alkyl having 1 to 8 carbon atoms or —CH$_2$—Ar;
Ar is phenyl or substituted phenyl, and at least one of $R_1$, $R_2$, $R_3$, $R_4$, $R_5$ and $R_6$ is other than —H.

Effective amounts of one or more of the compounds of formula I, as well as 6H-dibenzo[b,d]pyran-6-one, in combination with a suitable carrier may be used as inhibitors of mutagenic activity. The novel compounds may also exhibit protective characteristics against the normal tissue toxicity caused by certain alkylating agents used in cancer chemotherapy.

The compounds, in accordance with an aspect of this invention, may be prepared by using the methodology of aromatic-directed metalation in conjunction with transition-metal catalyzed cross-coupling reactions to prepared the desired reactants. The process comprises converting a compound of the following formula II

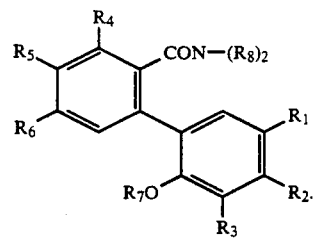

II wherein:
$R_1$ is —H, —OH or —OR' or

$R_2$ is —H, —OH or —OR' or

$R_3$ is —H, —OH or —OR' or

$R_4$ is —H, —OH or —OR' or

$R_5$ is —H, —OH or —OR' or

$R_6$ is —H, —OH or —OR' or

$R_7$ is lower alkyl having 1 to 8 carbon atoms,
$R_8$ is ethyl or isopropyl,
R' is lower alkyl having 1 to 8 carbon atoms or —CH$_2$—Ar when Ar is phenyl or substituted phenyl, under suitable reactions conditions to yield the desired compound of formula I. $R_1$, $R_2$, $R_3$, $R_4$, $R_5$ and $R_6$ of formula II are selected to produce the desired compound where optionally any remaining alkoxy groups are wholly or partially converted to hydroxyl groups as desired, or any hydroxyl groups are wholly or partially converted to alkoxy groups.

BRIEF DESCRIPTION OF THE DRAWINGS

FIG. 1 is a graph showing the inhibition effectiveness of ellagic acid (solid line) and the ellagic acid derivative 3,4,7,8-tetrahydroxy-6H-dibenzo-[b,d]pyran-6-one, and FIG. 2 is a graph showing the inhibition effectiveness of two other derivatives according to this invention.

DETAILED DESCRIPTION OF THE PREFERRED EMBODIMENTS

The novel compounds, according to this invention, belong to the family of biaryl compounds. These compounds may be produced by a cross-coupling method. The novel compounds are represented by the following formula I:

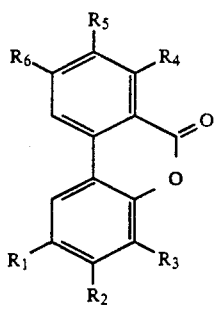

wherein:
- $R_1$ is —H, —OH or —OR';
- $R_2$ is —H, —OH or —OR';
- $R_3$ is —H, —OH or —OR';
- $R_4$ is —H, —OH or —OR';
- $R_5$ is —H, —OH or —OR';
- $R_6$ is —H, —OH or —OR';
- R' is lower alkyl having 1 to 8 carbon atoms or —CH$_2$—Ar;
- Ar is phenyl or substituted phenyl, and at least one of $R_1$, $R_2$, $R_3$, $R_4$, $R_5$ and $R_6$ is other than —H.

Preferred novel compounds represented by formula I are as follows:

7-hydroxy-6H-dibenzo[b,d]pyran-6-one
3,7-dimethoxy-6H-dibenzo[b,d]pyran-6-one
3,4-dihydroxy-6H-dibenzo[b,d]pyran-6-one
3-hydroxy-4-methoxy-6H-dibenzo[b,d]pyran-6-one
3-methoxy-4-hydroxy-6H-dibenzo[b,d]pyran-6-one
3,4,7,8-tetrahydroxy-6H-dibenzo[b,d]pyran-6-one and a variation of hydroxy substitution for $R_1$, $R_2$, $R_3$, $R_4$, $R_5$ and $R_6$ where:

e) one of, two of or all three of $R_1$, $R_2$ and $R_3$ are —OH and any remaining of $R_1$, $R_2$ and $R_3$ are all of $R_4$, $R_5$ and $R_6$ are —H, ii) one of, two of or all three of $R_4$, $R_5$ and $R_6$ are —OH and any remaining of $R_4$, $R_5$ and $R_6$ and all of $R_1$, $R_2$ and $R_3$ are —H, and iii) one or more of $R_1$, $R_2$, $R_3$, $R_4$, $R_5$ and $R_6$ are —OH and any remaining of $R_1$, $R_2$, $R_3$, $R_4$, $R_5$ and $R_6$ are —H.

These compounds and others represented by formula I, along with the compound 6H-dibenzo[b,d]pyran-6-one wherein formula I, $R_1$, $R_2$, $R_3$, $R_4$, $R_5$ and $R_6$ are all —H exhibit inhibition properties regarding mutagenic activity in living cells. As well, the compounds may be particularly useful as a protective agent against the normal tissue toxicity caused by certain alkylating agents used in cancer chemotherapy. The compounds are particularly suitable as inhibitors of the mutagenicity of polycyclic aromatic hydrocarbons and dialkyl nitrosamines. Polycyclic aromatic hydrocarbon metabolites include the known compound BPDE (benzo[a]pyrine-7,8-dihydrodiol-9,10-epoxide). An example of the nitrosamine group is dimethylnitrosamine.

The compounds are preferably made by converting compounds of the following formula II into the desired ellagic acid congeners.

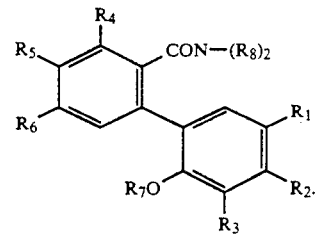

wherein:
$R_1$ is —H, —OH or —OR' or

$R_2$ is —H, —OH or —OR' or

$R_3$ is —H, —OH or —OR' or

$R_4$ is —H, —OH or —OR' or

$R_5$ is —H, —OH or —OR' or

$R_6$ is —H, —OH or —OR' or

$R_7$ is lower alkyl having 1 to 8 carbon atoms,
$R_8$ is ethyl or isopropyl,
R' is lower alkyl having 1 to 8 carbon atoms or —CH$_2$—Ar when Ar is phenyl or substituted phenyl, In converting the selected compound of formula II into the compound of formula I, a reorientation of the molecules takes place to complete the pyran ring by coupling with the —O of the $R_7$ substituent. The substituent positions $R_1$, $R_2$, $R_3$, $R_4$, $R_5$ and $R_6$ of formula II therefore become the same substituents of formula I when conversion is completed. When the prepared compound of formula I has one or more alkoxy groups, the resultant compound may be treated to hydrolyse wholly or partially the alkoxy groups to hydroxyl groups by way of acid hydrolysis. A suitable acid for converting the alkoxy groups is acetic acid.

It is appreciated that wholly or partially hydrolyzing the methoxy substituents means converting all the methoxy groups to hydroxyl groups or just converting some of the methoxy groups to the hydroxyl groups. Such partial conversion of methoxy groups can be made selective to substituent position depending on the conditions of the reaction and the positioning of the substituents to be converted.

Conversely, the hydroxyl groups of the prepared compound may be wholly or partially methoxylated to methoxy groups in accordance with standard procedures and reactive conditions. Such partial methoxylation may be selective as to substituent position depending on the reaction conditions chosen and the positioning of the substituents to be converted.

It is appreciated that the compounds of formula II may be synthesized by various techniques. However, the preferred approach, according to this invention, is the synthesis of such compounds by cross-coupling, as disclosed by Sharp and Snieckus in "Synthetic Connections to the Aromatic Directed Metalation Reaction, Unsymmetrical Biaryls by Palladium-Catalyzed Cross-Coupling of Directed Metalation-Derived Arulboronic Acids with Aryl Halide" 1985, Tetrahedron Letters, Volume 26, #49, pages 5997–6000. The catalyzed cross-coupling reactions of this reference prepare the compounds of formula II. A preferred aspect of the invention in preparing the compounds of formula II is exemplified by the following reaction scheme.

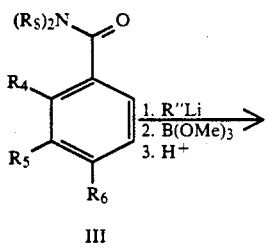

III

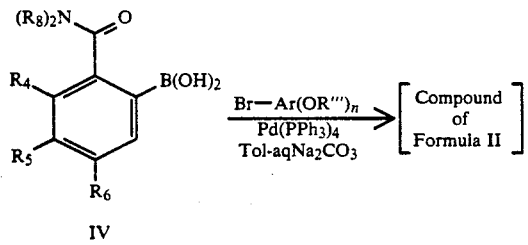

IV wherein:

$R_4$, $R_5$ and $R_6$ are as defined in above formula II,
R' is as defined in formula II,
R" is sec-butyl or t-butyl,
$R_1$ is —H, —OH or —OR' or

—CH

Me is methyl,
Ar is phenyl,
n is 1, 2 or 3.

A compound of formula III is subjected to the ortho-metalation technique followed by trimethylborate treatment to produce the compound of formula IV. The solid carboxamido phenyl boronic acid of formula IV can be prepared in 80% overall yield by the ortho-metalation technique and treatment with B(OMe)₃ followed by an acidic work-up; for example with the use of 5% AqHCl.

The compound of formula IV is then subjected to the cross-coupling procedure of Suzuki et al *A. Syn. Commun.* 1981, 11, 513. The desired aryl group is then inserted in place of the boronic acid B(OH)₂. By suitable selection of the substituents for the Ar group, the appropriate compounds of formula II are thus prepared. This selection is indicated by the (RO)ₙ group.

The preferred conversion of the compounds of formula II is achieved at low temperature by use of BBr₃ in dry methylene chloride solvent. The reaction is commenced at a very low temperature in the range of −75° C. to −80° C. Any of the remaining alkoxy groups at the substituent positions which are unwanted are converted to hydroxyl groups by treatment with a suitable acid, such as acetic acid.

The following Examples demonstrated preferred embodiments of the invention which are understood to be non-limiting with respect to the invention as defined in the appended claims.

EXAMPLE 1

Preparation of (N,N-Diisopropyl-2-carboxamido phenyl)boronic acid of Formula IV

To a stirred solution of s-BuLi-TMEDA (1.1 equip. 40 mmol) in 800 ml of THF (tetrahydrofuran) at −78° C., under dry argon atmosphere, was slowly added N,N-diisopropylbenzamide (35.6 mmol). The resulting light yellow solution was stirred at −78° C. for 45 minutes followed by addition of B(OMe)₃ (107 mmol). The reaction was allowed to warm up to room temperature over the period of twelve hours. pH of the reaction was adjusted in the range of 5–6, using 5% HCl. All the THF was evaporated. The aqueous layer was extracted with methylene chloride to give crude boronic acid in 95% yield.

EXAMPLE 2

Preparation of N,N-Diisopropyl-2,3,4-trimethoxy-2-biphenylcarboxamide of Formula II To a stirred suspension of tetrakistriphenylphosphinepalladium (0.35 mmol) in DME (dimethoxyethane) (20 ml), under argon atmosphere was added 2,3,4-trimethoxybromobenzene (4.2 mmol). The mixture was stirred at room temperature for 15 minutes followed by addition of 2 M Na₂CO₃ (4.2 ml) and an ethanolic (5 ml) solution of (N,N-diisopropyl-2-carboxamido phenyl) boronic acid (6.3 mmol). The reaction mixture was allowed to reflux for 11 hours. Evaporating the solvents under vacuum gave black gummy material which was worked up with methylene chloride. Evaporation of the solvent gave a yellow solid which on silica gel medium pressure column chromatograph (EtOAc-hexane; 1:1 v/v) yielded 93% (3.5 mmol) of the product. The product was recrystallized from: EtOAc-Hexane (m.p. 155° C.–160° C.). NMR spectrum was analyzed to be: δ0.71 (d, 3H, J=6.7 Hz, CH₃CH), 0.99 (d, 3H, J=6.7 Hz, CH₃CH), 1.23 (d, 3H, J=6.7 Hz, CH₃CH), 1.50 (d, 3H, J=6.7 Hz, CH₃CH), 3.28 (m, 1H, J=6.7 Hz CHCH₃)₂), 3.67 (m, 1H, J=6.7 Hz CHCH₃)₂), 3.82, 3.86, 3.87 (d, 9H, OCH₃), 6.66 (d, 1H, J=8.7 Hz, 5'H), 7.17 (d, 1H, J=8.7 Hz, 6'H), 7.26–7.39 (m, 4H, Ar—H); MS m/z (relative intensity) 371 (M⁺, 20), 340 (8), 270 (100), 256 (30), 241 (11), 212 (5).

EXAMPLE 3

Preparation of 3,4-Dihydroxy-6-H-dibenzo(b,d)pyran-6-one of Formula I

N,N-Diisopropyl-2',3',4'-trimethoxy-2-biphenylcarboxamide (0.94 mmol) was dissolved in dry methylene chloride (40 ml). The solution was cooled down to −78° C., BBr$_3$ (5.6 mmol) was added slowly. Reaction was allowed to warm to room temperature over a period of 22 hours. The mixture was again cooled down to −78° C. and methanol (3 ml) was added. The reaction was warmed to room temperature over a period of 2 hours. All solvent was evaporated. The solid was extracted with chloroform. Removal of solvent gave white fluffy solid which was dissolved in glacial acetic acid (10 ml) and refluxed over night. Removal of acetic acid gave a solid, which was worked up with chloroform-water, the aqueous layer was separated and was extracted several times with chloroform. The chloroform layer was washed with satd. NaHCO$_3$ solution. Removal of chloroform gave 77% (0.72 mmol) of solid product, which was recrystallized from methanol (m.p. 252° C.-254° C.). NMR spectrum was analyzed to be: δ6.84 (d, 1H, J=8.7 Hz, Ar—$\underline{H}$), 7.63 (d, 1H, J=8 Jz, Ar—$\underline{H}$), 7.82-7.89 (m 1H, Ar—$\underline{H}$), 8.17-8.24 (t, 2H, Ar—$\underline{H}$), 9.27 (br s, 1H, OH [D$_2$O exchangeable]), 9.89 (br s, 1H, OH [D$_2$O exchangeable]); MS m/z (relative intensity) 229 (M+1, 13), 228 (M+, 100), 200 (6), 126 (11), 115 (26).

EXAMPLE 4

Mutagenic Activity Inhibition Action Comparison of Ellagic Acid to Compounds of this Invention BPDE (benzo[a]pyrene-7,8-dihydrodiol-9,10-epoxide was purchased from the NCI Carcinogen Standard Reference Repository. BPDE was dissolved in dry THF/triethylamine (20/1) and stored at −20° C. The BPDE concentration was determined by UV absorbance measurement. For the Ames test, BPDE stock was diluted in DMSO (dimethylsulfoxide) immediately before addition to the incubation mix. Ellagic acid or a derivative according to this invention was dissolved in DMOS. The Ames assay protocol was based on that of Wood et al (supra). Bacteria were incubated with ellagic acid or the selected derivative of this invention for 1 minute at 37° C. BPDE was added and the mixture was incubated for 5 min at 37+ C. before addition of top agar and plating. Plates were incubated for 48 hours at 37° C. and the revertant colonies were counted with an automatic counter. Toxicity was monitored by examination of the background auxotrophic lawns, under a lower power microscope. Experiments were carried out with strains TA98 and TA100.

The inhibiting action of ellagic acid and the derivatives 3,4,7,8-tetrahydroxy-6H-dibenzo[b,d]pyran-6-one are invention was shown in FIG. 1. The addition of increasing concentrations of ellagic acid or the derivative of this invention gave a corresponding decrease in the number of revertant colonies. These test results exemplify that the compounds of formula I inhibit the mutagenic activity and in particular of polycyclic aromatic hydrocarbon metabolite, such as BDPE. Other derivatives, according to this invention, were tested in a similar manner to the above to determine their activity. The tested derivatives were 3,4-dihydroxy-6H-dibenzo[b,d]pyran-6-one and 3-methoxy-4-hydroxy-6H-dibenzo[b,d]pyran-6-one.

Tests have also been conducted to demonstrate that the compounds of this invention exhibit the property of inhibiting DNA damage induced by alkylating agents in mammalian cells which are used in cancer chemotherapy.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A compound of the following formula I:

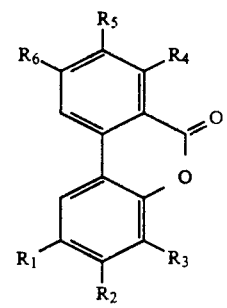

wherein:
R$_1$ is —H, —OH or —OR';
R$_2$ is —H, —OH or —OR';
R$_3$ is —H, —OH or —OR';
R$_4$ is —H, —OH or —OR';
R$_5$ is —H, —OH or —OR';
R$_6$ is —H, —OH or —OR'; and
R' is methyl or benzyl, and at least one of R$_1$, R$_2$, R$_3$, R$_4$, R$_5$ and R$_6$ is other than —H.

2. A compound of claim 1 of formula I wherein:
R$_1$ is —H, —OH or —OR';
R$_2$ is —H, —OH or —OR';
R$_3$ is —H, —OH or —OR';
R$_4$ is —H, —OH or —OR';
R$_5$ is —H, —OH or —OR';
R$_6$ is —H, —OH or —OR'; and
R' is benzyl and at least one of R$_1$, R$_2$, R$_3$, R$_4$, R$_5$ and R$_6$ is other than —H.

3. The compound 7-hydroxy-6H-dibenzo[b,d]pyran-6-one, represented by formula I wherein R$_1$, R$_2$, R$_3$, R$_5$ and R$_6$ are —H and R$_4$ is —OH.

4. The compound 3,7-dimethoxy-6H-dibenzo[b,d]pyran-6-one of claim 1 formula I, wherein R$_2$ and R$_4$ are —OCH$_3$ and R$_1$, R$_3$, R$_5$ and R$_6$ are —H.

5. The compound 3,4 dihydroxy-6H-dibenzo[b,d]pyran-6-one of claim 1, represented by formula I wherein R$_2$ and R$_3$ are —OH and R$_1$, R$_3$, R$_5$ and R$_6$ are —H.

6. The compound 3-methoxy-4-hydroxy-6H-dibenzo[b,d]pyran-6-one of claim 1, represented by formula I wherein R$_2$ is —OCH$_3$, R$_3$ is —OH and R$_1$, R$_4$, R$_5$ and R$_6$ are both —H.

7. The compound 3,4,7,8-tetrahydroxy-6H-dibenzo[b,d]pyran-6-one of claim 1, represented by formula I wherein R$_2$, R$_3$, R$_4$ and R$_5$ are —OH and R$_1$ and R$_6$ are —H.

8. A compound of claim 1 formula I wherein R$_1$, R$_4$, R$_5$ and R$_6$ are —H, R$_2$ is —OH and R$_3$ is —OCH$_3$.

9. A composition effective for inhibiting mutagenic activity in living cells comprises an effective amount of one or more compounds of the following formula I in conjunction with a suitable carrier:

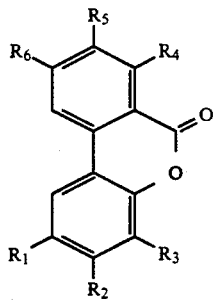

wherein:
$R_1$ is —H, —OH or —OR';
$R_2$ is —H, —OH or —OR';
$R_3$ is —H, —OH or —OR';
$R_4$ is —H, —OH or —OR';
$R_5$ is —H, —OH or —OR';
$R_6$ is —H, —OH or —OR';
R' is methyl or benzyl, and at least one of $R_1$, $R_2$, $R_3$, $R_4$, $R_5$ and $R_6$ is other than —H.

10. A composition of claim 9 effective for inhibiting mutagenic activity in living cells wherein the active compound is selected from the group represented by formula I, wherein one of, two of or all three of $R_1$, $R_2$ and $R_3$ are —OH and any remaining of $R_1$, $R_2$ and $R_3$ and all of $R_4$, and $R_5$ and $R_6$ are —H, in conjunction with a suitable carrier.

11. A composition of claim 9 effective for inhibiting mutagenic activity in living cells wherein the active compound is selected from the group represented by formula I, wherein one of, two of or all three of $R_4$, $R_5$, $R_6$ are —OH and any remaining of $R_4$, $R_5$ and $R_6$ and all of $R_1$, $R_2$ and $R_3$ are —H, in conjunction with a suitable carrier.

12. A composition of claim 9 effective for inhibiting mutagenic activity in living cells wherein the active compound is selected from the group represented by formula I, wherein one or more of $R_1$, $R_2$, $R_3$, $R_4$, $R_5$ and $R_6$ are —OH and any remaining of $R_1$, $R_2$, $R_3$, $R_4$, $R_5$ and $R_6$ are —H, in conjunction with a suitable carrier.

13. A composition of claim 9 wherein the active compound is 7-hydroxy-6H-dibenzo[b,d]pyran-6-one.

14. A composition effective for inhibiting mutagenic activity in living cells wherein the active compound is 3,7-dimethoxy-6H-dibenzo[b,d]pyran-6-one, in conjunction with a suitable carrier.

15. A composition of claim 10 wherein the active compound is 3,4-dihydroxy-6H-dibenzo[b,d]pyran-6-one.

16. A composition effective for inhibiting mutagenic activity in living cells wherein the active compound is 3-methoxy-4-hydroxy-6H-dibenzo[b,d]pyran-6-one, in conjunction with a suitable carrier.

17. A composition of claim 12 wherein the active compound is 3,4,7,9-tetrahydroxy-6H-dibenzo[b,d]pyran-6-one.

18. A composition effective for inhibiting mutagenic activity in living cells comprising an effective amount of 6H-dibenzo[b,d]pyran-6-one in combination with a pharmaceutically acceptable carrier.

* * * * *

UNITED STATES PATENT AND TRADEMARK OFFICE
CERTIFICATE OF CORRECTION

PATENT NO. : 5,104,894
DATED : April 14, 1992
INVENTOR(S) : Philip D. Josephy and Victor A. Snieckus It is certified that error appears in the above-identified patent and that said Letters Patent is hereby corrected as shown below:

At column 1, line 8, delete "for" and substitute --or-- therefore.

At column 1, line 16, after "1982" insert --,-- and after "PNAS" delete ":".

At column 1, line 18, delete "benzo[a]pyrine" and substitute --benzo[a]pyrene-- therefore.

At column 1, line 21, delete "1663-16667" and substitute --1663-1667-- therefore.

At column 1, line 67, delete "prepared" and substitute --prepare-- therefore.

At column 3, line 45, delete "e)" and substitute --i)-- therefore.

At column 3, line 47, delete "are" and substitute --and-- therefore.

At column 3, line 67, delete "pyrine-7,8-dihydrodiol-9,10-epoxide)" and substitute --pyrene-7,8-dihydrodiol-9,10-epoxide)-- therefore.

At column 4, line 57, delete "molecules" and substitute --molecule-- therefore.

At column 6, line 27, delete "equip." and substitute --equiv.-- therefore.

UNITED STATES PATENT AND TRADEMARK OFFICE
CERTIFICATE OF CORRECTION

PATENT NO. : 5,104,894

DATED : April 14, 1992

INVENTOR(S) : Philip D. Josephy and Victor A. Snieckus

It is certified that error appears in the above-identified patent and that said Letters Patent is hereby corrected as shown below:

At column 7, line 46, delete "DMOS" and substitute --DMSO-- therefore.

At column 7, line 50, delete "37+" and substitute --37°-- therefore.

Signed and Sealed this

Seventeenth Day of August, 1993

Attest:

BRUCE LEHMAN

Attesting Officer

Commissioner of Patents and Trademarks